United States Patent [19]

Barrington

[11] 4,160,446

[45] Jul. 10, 1979

[54] APPARATUS FOR AND METHOD OF STERILIZATION BY THE DELIVERY OF TUBAL-OCCLUDING POLYMER

[75] Inventor: James E. Barrington, Woburn, Mass.

[73] Assignee: Abcor, Inc., Wilmington, Mass.

[21] Appl. No.: 823,929

[22] Filed: Aug. 12, 1977

[51] Int. Cl.² ............................................. A61B 19/00
[52] U.S. Cl. .................................. 128/1 R; 128/349 B
[58] Field of Search ................... 128/235, 1 R, 349 B, 128/260

[56] References Cited

U.S. PATENT DOCUMENTS

| 3,822,702 | 7/1974 | Bolduc et al. | 128/235 |
| 3,871,374 | 3/1975 | Bolduc et al. | 128/235 |
| 3,875,939 | 4/1975 | Bolduc et al. | 128/235 |
| 3,948,259 | 4/1976 | Bolduc et al. | 128/235 |
| 3,972,331 | 8/1976 | Bolduc et al. | 128/235 |

*Primary Examiner*—John D. Yasko
*Attorney, Agent, or Firm*—Richard P. Crowley

[57] ABSTRACT

A device for the delivery of a tubal-occluding polymer for sterilization of females, which device comprises a plurality of concentric tubes with a two-compartment balloon at the one end thereof.

12 Claims, 7 Drawing Figures

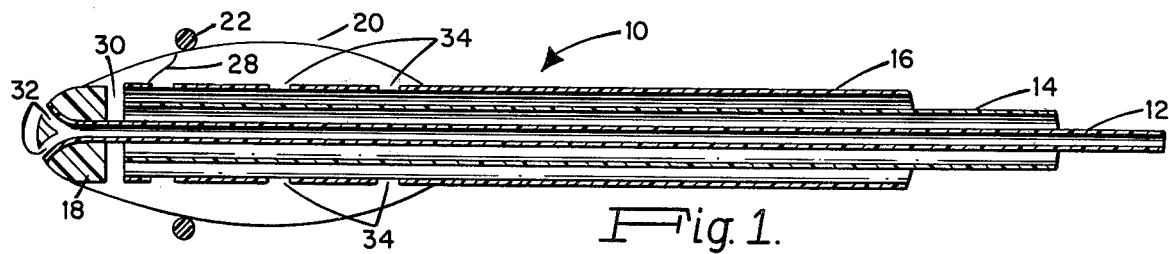
Fig. 1.
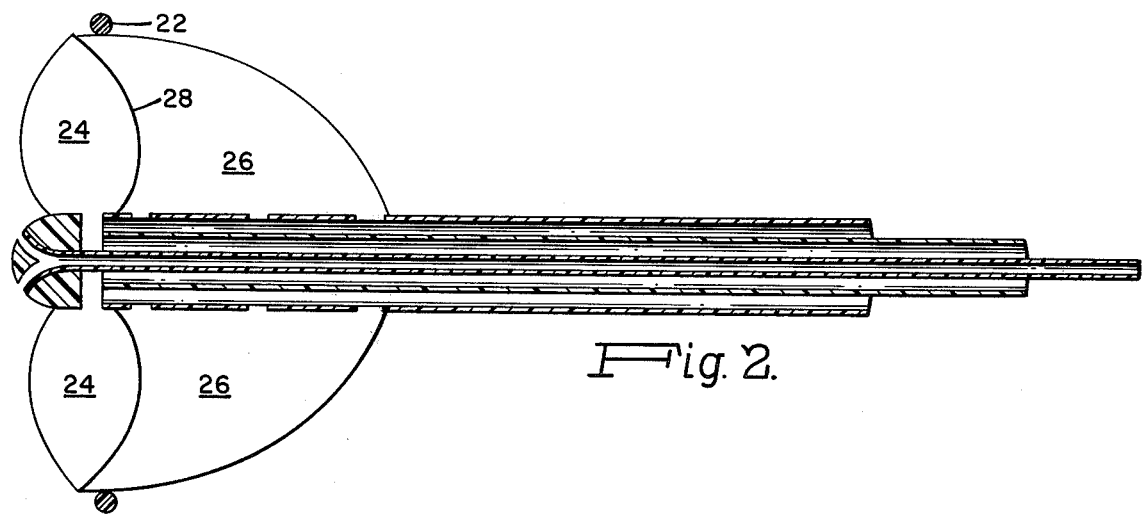
Fig. 2.
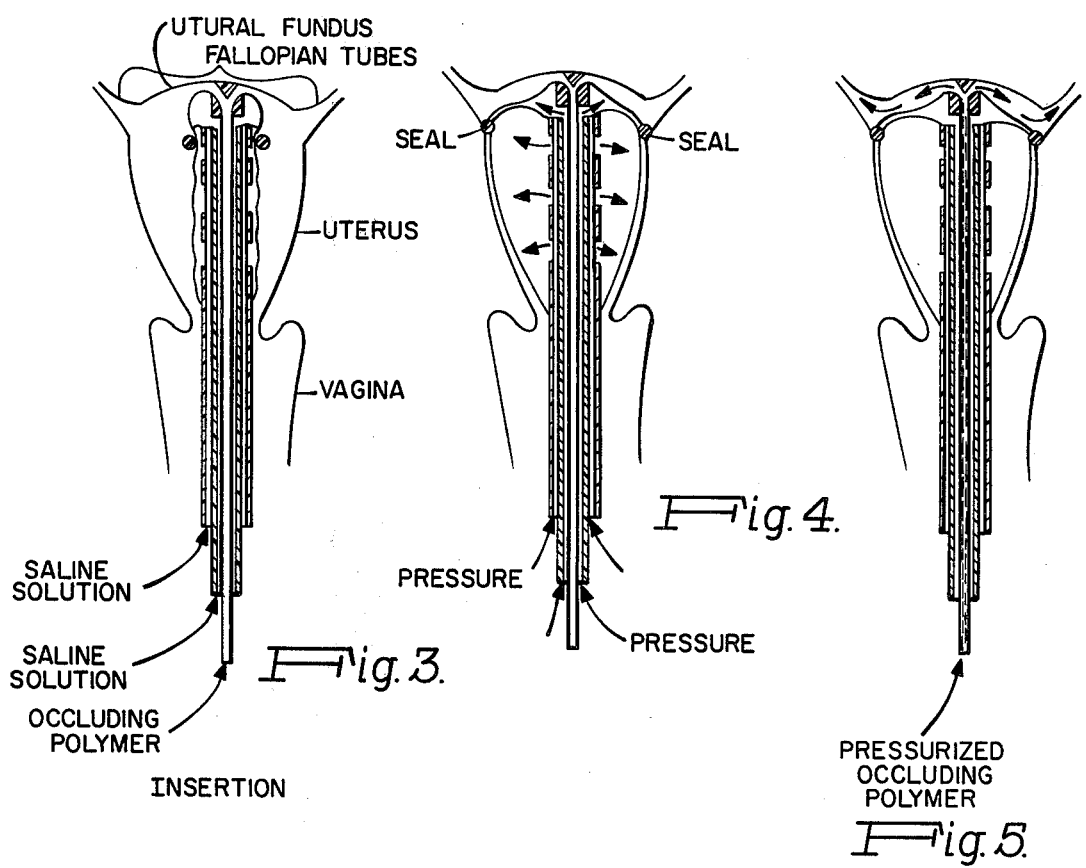
Fig. 3.
Fig. 4.
Fig. 5.

PRESSURE

SECONDARY PRESSURIZATION
OF DISTAL CHAMBER

OCCLUDED FALLOPIAN TUBES
AFTER DEFLATION & REMOVAL

APPARATUS FOR AND METHOD OF STERILIZATION BY THE DELIVERY OF TUBAL-OCCLUDING POLYMER

BACKGROUND OF THE INVENTION

One method of achieving the sterilization of a female, particularly a human female, is the transcervical introduction of tissue adhesives or tissue-occluding and -destroying agents to occlude or destroy the fallopian tubes. A contrast-pressure technique for female sterilization has been suggested, wherein balloon cannulae have been used to introduce and confine material into the cornua and the fallopian tubes, and an organosilicon polymer or rubber has been suggested as a tubal-occluding agent (See "The Contrast Pressure Technique for Female Sterilization" by Thomas S. Moulding et al, Contraception, May 1976, Vol. 13, No. 5, pages 547–557).

An instrument-delivery system for the delivery consistently of low-viscosity material to the interstitial and isthmic portions of the fallopian tubes in an outpatient technique has been described (see "Single-application Fertility-regulating Device: Description of a New Instrument", Am. J. Obstet. Gynecol., Jan. 1, 1977, pages 86–90, Ralph M. Richart et al). However, this device is not wholly satisfactory in that it is a relatively complex mechanical device of high cost, and is not adapted for the delivery and use of polymeric-occluding agents.

SUMMARY OF THE INVENTION

My invention relates to an apparatus and a system for the delivery of tubal-occluding agents, such as a polymer, and to a method of sterilization by employing a tubal-occluding polymer. More particularly, my invention is directed to a balloon-type cannulae apparatus for the transcervical introduction simultaneously of a medically acceptable, expandable, polymeric-occluding agent to both fallopian tubes, and to a method of human female sterilization by forcing into the fallopian tubes an expandable, polymeric, tubal-occluding agent.

My invention particularly is directed to the delivery-head portion of the apparatus and system to deliver via the uterus and cornua a tubal-occluding polymer for sterilization purposes into the fallopian tubes. My apparatus is relatively simple and may be used on an outpatient basis, and does not require special training and special positioning relative to the cornua of the fallopian tubes. Since no special positioning is required, my apparatus is simple in use and minimizes training needed by an administrator, and obviates the need for special viewing devices, such as hysteroscopes and X-ray equipment. My apparatus and method also reduce the time for effecting sterilization by delivering effectively and simultaneously the occluding polymer to both fallopian tubes. My apparatus, system and method have numerous other advantages, and permit the rapid, simple and low-cost sterilization of females.

In my method of occluding the fallopian tubes, a polymer-occluding delivery apparatus, having a delivery head, is transcervically inserted into the uterus via the vagina, the delivery head comprising a balloon-cannula device, the balloon being in a relaxed condition during insertion; sealing the balloon against the internal wall of the uterine cavity by inflation of the balloon; depositing a tubal-occluding agent, such as an occluding polymer like an expandable, soft, resilient, medically acceptable, foamable polymer, through the balloon-cannula and delivery-head device into the sealed area of the uterus and typically against the interior wall of the uteral fundus; and, thereafter, forcing simultaneously the deposited polymer into the fallopian tubes, such as by the expansion of another compartment of the balloon; and, thereafter, deflating the balloon of the delivery device and withdrawing the balloon cannula from the uterus. In my method, a portion of the uterine cavity is sealed through the inflation of a balloon therein, the expandable polymer disposed by a delivery head against the interior wall of the uterus fundus, and, thereafter, the polymer so deposited is forced outwardly by a further balloon inflation, so that the polymer simultaneously, through pressure of the expanding balloon, is forced into the ends of the fallopian tubes.

My apparatus and system will be described in particular in connection with the delivery of an occluding polymer; however, such occluding polymer typically may be a polymer subject to flow by pressure, so as to flow into the fallopian tubes and to occlude the tubes. In particular, I have found that a medically acceptable polymer, such as an organosilicon rubber, and particularly a foamable polymer, wherein the foam comprises a resilient, semi-rigid, closed-cell foam, may be employed in my device; although it is recognized and is a part of my invention that my apparatus may be used to deposit other materials and other tissue-destroying and -occluding agents into the uterine cavity, but is specifically designed and useful for the introduction of polymeric-occluding agents.

My balloon-cannula device comprises three concentric tubes, with a two-chambered, expandable, balloon sheath affixed to the outermost tube at the distal end thereof, the balloon sheath being capable of moving between a relaxed noninflated condition, which permits the insertion of the concentric tubes into the uterine cavity, and an expanded inflated condition. The central innermost tube is adapted and designed to deliver the occluding polymer, or other material, via orifices located in the blunt distal end cap. The outermost tube delivers a fluid, typically a gas or liquid, but more particularly an aqueous saline solution, to pressurize the balloon to effect, firstly, the sealing of the uterine cavity. The balloon may be annulated by the employment of an O-sealing ring or other means. The middlemost tube delivers a fluid, particularly an aqueous saline solution, to expand the other chamber of the balloon. After delivery of the occluding polymer, the expansion of the second chamber of the balloon forces outwardly and simultaneously the polymer deposited against the interior wall of the uteral fundus and into the opening of each fallopian tube.

Delivery of the occluding polymer or other material and of the fluid to expand the balloon may be accomplished by pressurizing in the appropriate sequence the fluid and polymer, such as by employing a three-plunger-type syringe operatively connected to each compartment by the appropriate concentric tube, so that, after insertion of the delivery head of the balloon cannula into the uterus, the operator may push the plunger, firstly, to seal the chamber; secondly, to deliver the occluding polymer; and, thirdly, to force the polymer into the fallopian tubes.

My apparatus and system, thereby, permit the delivery of a tubal-occluding polymer into the fallopian tubes for sterilization purposes on an outpatient basis, and are characterized by simplicity in operation and low cost.

BRIEF DESCRIPTION OF THE DRAWINGS

FIG. 1 is a representative sectional view of my balloon-cannula apparatus showing the balloon in the relaxed condition;

FIG. 2 is a representative sectional view of my balloon-cannula apparatus showing both compartments of the balloon in the inflated condition; and FIGS. 3-7 illustrate the sequential steps in the use of my balloon-cannula apparatus by delivery of an occluding polymer into the fallopian tubes.

DESCRIPTION OF THE EMBODIMENTS

Figure 6:
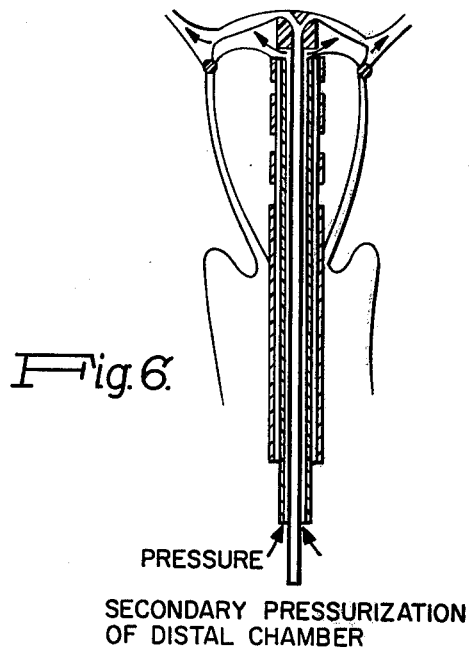

Referring in particular to FIGS. 1 and 2, my apparatus 10 comprises three, concentrically arranged, elongated, semirigid, concentric tubes 12, 14 and 16, with a two-chamber 24 and 26 expandable and contractable, resilient, elastomeric, balloon sheath 20, with an inner wall 28 affixed to the distal end of the outermost tube 16. Secured to the distal end of innermost tube 12 is a delivery head 18, with a Y-tubular orifice 32. The innermost tube 12 is adapted to deliver an occluding polymer through the tube and delivery head 18 and orifice 32 into a sealed uterine cavity. The distal-delivery head 18 is rounded and blunt, so that the delivery head may contact the interior wall of the uteral fundus on insertion without injury. Tube 16 is adapted to deliver a fluid, such as a gas or a liquid, to pressurize the balloon 20, and particularly chamber 26 through orifice 34, to form a seal within the uterine cavity. The balloon 20 is annulated by a peripheral elastic or resilient-type O-ring seal 22. Tube 14 is adapted to deliver a gas or liquid through orifice 30 to pressurize the distal balloon chamber 24, which on expansion forces the occluding polymer, delivered from heat 18, into the fallopian tubes.

Referring in particular to FIGS. 3-7, FIG. 3 shows my apparatus 10 in combination with a source of occluding polymer and an aqueous saline solution for pressurizing the balloon element 20. For illustration purposes only, FIG. 3 shows the insertion of my apparatus 10 transcervically inserted into the uterus via the vagina, until the blunt end of the delivery head 18 is in contact with the interior wall of the uteral fundus, and with the balloon 20 in a relaxed condition.

FIG. 4 illustrates the pressurization of chamber 26 of the balloon 20 by the use of the pressurized saline solution by passage from the source through the tube 16, with the balloon 20 expanding with full pressurization of the proximal chamber 26, and only partial pressurization of the distal chamber 24. The pressurized proximal chamber 26 is placed in a sealing relationship with the interior wall of the uterus, with O-ring 22 forming a seal with the uterine wall. The distal chamber 24 is pressurized by the use of a pressurized saline solution through the tube 14, until the chamber 24 is mostly inflated, but does not press firmly against the interior wall of the uteral fundus.

FIG. 5 illustrates the delivery of a pressurized occluding polymer from the source through tube 12 and through the delivery head 18 and orifice 32 into the area of the interior wall of the uteral fundus, which is adjacent to the position of head 18. A premeasured amount of an occluding, flowable, expandable polymer, such as a catalyzed organosilicon rubber or polymer containing a blowing agent, is delivered under pressure, such as, for example, by the employment of a syringe, with delivery of the polymer through tube 12. One polymer employed is a medically acceptable, catalyzed, silicon polymer which contains a blowing agent, and which slowly expands to form a resilient, semirigid, closed-cell, silicon-polymer foam; although other polymers can be used.

FIG. 6 shows the further pressurization of the distal-balloon chamber 24, which, as it expands by further pressurization, forces the deposited occluding polymer through the cornua and into the fallopian tubes, thereby accomplishing polymerization and resulting sterilization by tubal occlusion on curing of the expanded polymer.

Figure 7:
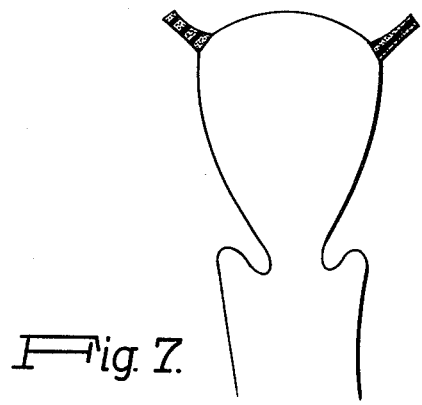

FIG. 7 is a representation of the occluded fallopian tubes after deflation of both the balloon 20 and chambers 24 and 26, and the withdrawal of the balloon-cannula apparatus 10. The fallopian tubes plug with the cured or catalyzed closed-cell, resilient, sealing, organosilicon polymer, such as an elastomeric silicon polymer.

As illustrated and described, my apparatus is directed to the delivery of a tubal-occluded expandable polymer for female sterilization through the steps of insertion of the apparatus; full pressurization of the proximal chamber and partial pressurization of the distal chamber to effect a seal within the uterine cavity; the introduction of a pressurized, expandable, occluding polymer through the uteral fundus, the secondary pressurization of the distal chamber forcing the occluding polymer into the fallopian tubes; and the deflation and removal of my apparatus, leaving the fallopian tubes occluded with the cured, catalyzed polymer.

What I claim is:

1. An occluding-polymer delivery system for tubal sterilization by polymer occlusion of the fallopian tubes in a female, which apparatus comprises:
    (a) first, second and third elongated delivery tubes respectively and concentrically arranged, each tube having a one end and another end;
    (b) a resilient expandable balloon element secured about the one end of the third outermost delivery tube, the balloon element adapted to move between a relaxed noninflated condition and a pressurized inflated condition, the balloon element characterized by a first proximal chamber and a second distal chamber, each chamber separately inflatable;
    (c) a source of an occluding polymer;
    (d) means to introduce the occluding polymer from its source into the outer end of the first innermost tube and to discharge the polymer from a discharge head at the one end of the innermost tube;
    (e) a discharge head at the one end of the innermost tube;
    (f) a source of pressurized fluid;
    (g) means to introduce the pressurized fluid into the second and third tubes to effect the separate expansion of the first proximal and second distal chambers of the balloon-sheath element in a desired sequence; and
    (h) sealing means peripherally positioned about the balloon element and approximately between the proximal and distal chambers and which moves with the balloon element between an inflated and a noninflated position to provide for a seal between the inner wall of the uterus and the first proximal chamber in the inflated condition;
    whereby, on insertion of the delivery head into the uterine cavity, positioned approximately opposite the uteral fundus, the proximal and distal chambers may be inflated in sequency by the introduction of fluid from the source of fluid, firstly, to effect a seal between the interior wall of the uterus and the expanded balloon sheath, and, thereafter, to permit the introduction of an occluding polymer, and, thereafter, the forcing of the occluding polymer into the fallopian tubes by the full pressurization of the second distal chamber of the balloon-sheath element, and the subsequent deflation of both chambers and the withdrawal of the device from the uterus.

2. The system of claim 1 wherein the source of occluding polymer comprises a medically acceptable, catalyzed, expandable, occluding polymer which, after introduction and curing, forms a resilient, semirigid, closed-cell foam.

3. The system of claim 1 wherein the occluding polymer comprises a medically acceptable silicon polymer containing a curing system and a blowing agent.

4. The system of claim 1 wherein the source of fluid, to expand the balloon-sheath element, comprises an aqueous saline solution.

5. The system of claim 1 wherein the sealing means comprises an elastomeric-type O-ring peripherally positioned about the balloon sheath approximately between the first proximal and second distal chambers of the balloon element.

6. The system of claim 1 wherein the delivery head comprises a blunt-cap delivery-head element having two diversion orifices therein for the discharge of the occluding polymer toward each of the fallopian tubes of the female to be sterilized.

7. An occluding-polymer delivery apparatus for tubal sterilization of the fallopian tubes of a female, which apparatus comprises:
 (a) first, second and third elongated, cylindrical, delivery tubes respectively and concentrically arranged, each tube having a one end and another end;
 (b) a blunt-cap delivery head secured at the one end of the first tube;
 (c) a source of an expandable, occluding, medically acceptable, organosilicon polymer for introduction into and occlusion of the fallopian tubes;
 (d) means to introduce the polymer under pressure from the source into the one end of the first tube and to discharge the occluding polymer from the other end of the tube and the delivery head of the tube;
 (e) a source of an aqueous saline fluid;
 (f) means to introduce the saline fluid under pressure in a desired sequence into the one end of the second and third tubes;
 (g) an expandable balloon-sheath element formed of a resilient, inflatable, elastomeric material, the balloon element secured about the one end of the third outermost delivery tube, the balloon element characterized by first proximal and second separately inflatable chambers therein, the first proximal chamber inflatable by introduction of a saline solution into the one end of the third outermost tube, and the second distal chamber inflatable by the introduction of a saline solution into the other end of the second tube;
 (h) an O-ring means annularly positioned about the balloon-sheath element and adapted for movement with the balloon-sheath element between a relaxed noninflatable condition and a pressurized inflatable condition, the O-ring sealing means adapted to provide a seal between the interior wall of the uterus and the balloon-sheath element in the inflated condition,
 whereby a saline solution may be introduced to expand the proximal chamber into sealing contact with the interior wall of the uterus, and, thereafter, an occluding polymer discharged against the interior wall of the uteral fundus, and, thereafter, the distal chamber inflated by a saline solution to force the occluded polymer into the open ends of the fallopian tubes to effect sterilization.

8. A method of effecting sterilization in a female by polymer occlusion of the fallopian tubes of a female, which method comprises:
 (a) introducing into the uterine cavity a balloon-cannula element having at the one distal end thereon a two-compartment balloon composed of separately inflatable proximal and distal chambers in a relaxed condition, the balloon element having a peripheral sealing means approximately between the proximal and distal chambers, the cannula element composed of first, second and third tubes concentrically arranged, and a polymer-delivery head at the end of the first tube, with the polymer-delivery head positioned adjacent to the uteral fundus wall of the uterine cavity;
 (b) pressurizing the proximal chamber of the balloon-sheath element to inflate the proximal chamber and to effect a sealing relationship between the interior wall of the uterine cavity and the exterior surface of the balloon-sheath element, and partially pressurizing and partially inflating the distal chamber of the balloon-sheath element;
 (c) introducing a pressurized, expandable, occluding polymer through the polymer-delivery head, and depositing the polymer adjacent the uteral fundus;
 (d) pressurizing the distal chamber of the balloon-sheath element to inflate fully the distal chamber to force the deposited occluding polymer toward and laterally into the open end of the fallopian tubes of the female to be sterilized;
 (e) deflating the distal and proximal chambers; and
 (f) withdrawing the cannula balloon-sheath element from the uterus, thereby effecting sterilization of the female by occlusion of the fallopian tubes and by deposition and curing of the polymer therein.

9. The method of claim 8 wherein the occluding polymer comprises an expandable, curable, medically acceptable, silicon polymer.

10. The method of claim 8 which includes pressurizing and inflating the proximal and distal chambers employing a saline solution.

11. The method of claim 8 wherein the sealing means comprises a peripheral elastomeric O-ring positioned approximately between the proximal and distal chambers and which includes forcing the O-ring into a sealing relationship with the wall of the uterus on pressurization and inflation of the proximal chamber.

12. The method of claim 8 which includes introducing the polymer under pressure through a delivery head which directs the occluding polymer toward each of the open ends of the fallopian tubes.

* * * * *